United States Patent [19]

Okajima

[11] 4,138,013
[45] Feb. 6, 1979

[54] ENTERIC CAPSULES

[75] Inventor: Yakutaro Okajima, Fukazawa, Japan

[73] Assignee: Parke, Davis & Company, Detroit, Mich.

[21] Appl. No.: 805,763

[22] Filed: Jun. 13, 1977

Related U.S. Application Data

[63] Continuation of Ser. No. 718,297, Aug. 27, 1976, abandoned, which is a continuation-in-part of Ser. No. 568,974, Apr. 17, 1975, abandoned.

[51] Int. Cl.² .............................................. A61K 9/58
[52] U.S. Cl. .................................... 206/528; 106/128; 106/137; 106/189; 106/193 D; 106/197 R; 206/529; 260/8; 424/32; 424/35; 424/37; 427/3
[58] Field of Search ...................... 424/32, 33, 35, 37; 260/8; 220/8, 352; 427/3; 206/528, 529; 106/128, 137, 196, 189, 193 D, 197 R

[56] References Cited
U.S. PATENT DOCUMENTS

| 2,718,667 | 9/1955 | Malm et al. ............................ 424/35 |
| 3,826,666 | 7/1974 | Hirai et al. ............................ 106/128 |
| 3,859,228 | 10/1975 | Morishita et al. ..................... 424/35 |
| 4,001,390 | 1/1977 | Ohno et al. ............................ 424/32 |

Primary Examiner—Lorenzo B. Hayes
Attorney, Agent, or Firm—David B. Ehrlinger; Stephen Raines

[57] ABSTRACT

Pharmaceutical capsules with telescopically engaged body and cap portions, also known as hard shell capsules, having enteric properties. The capsule body and cap portions are formed by dip-molding using a homogeneous film-forming mixture comprising (1) hydroxypropyl methylcellulose and an ammonium salt of cellulose acetate phthalate polymer, or (2) gelatin and an ammonium salt of a copolymer of methacrylic acid and methacrylic acid alkyl ester; optionally with the inclusion of plasticizer and/or coloring agent. The capsules are soluble in or disintegrated by the alkaline intestinal secretions but are substantially insoluble or resistant to solution in the acid secretions of the stomach.

6 Claims, 1 Drawing Figure

U.S. Patent  Feb. 6, 1979  4,138,013
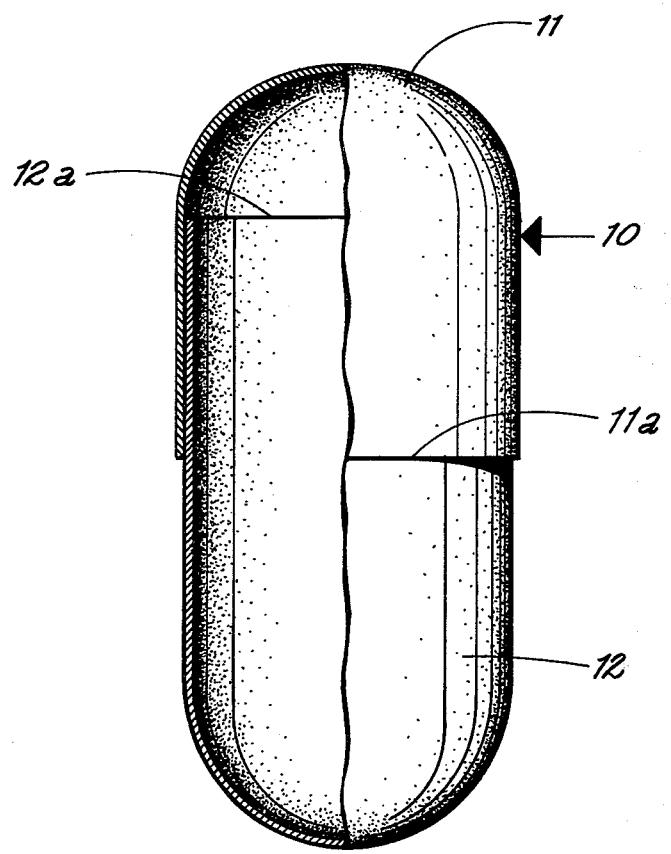

ENTERIC CAPSULES

This application is a continuation of prior United States application Ser. No. 718,297 filed Aug. 27, 1976, which in turn is a Continuation-In-Part of prior United States application Serial No.568,974 filed Apr. 17, 1975 both now abandoned.

SUMMARY AND DETAILED DESCRIPTION:

The present invention relates to enteric capsules. More particularly, the invention relates to pharmaceutical capsules having capsule body and cap portions formed by dipmolding using a homogeneous film-forming mixture comprising (1) gelatin and an ammonium salt of hydroxypropyl methylcellulose phthalate polymer, or (2) hydroxypropyl methylcellulose and an ammonium salt of cellulose acetate phthalate polymer, or (3) gelatin and an ammonium salt of a copolymer of methacrylic acid and methacrylic acid alkyl ester; optionally in combination with other ingredients; and to methods for the production of such pharmaceutical capsules.

As used herein, the term "enteric properties" means the properties of being soluble in or disintegrated by the alkaline intestinal secretions but being substantially insoluble or resistant to solution in the acid secretions of the stomach. The term "capsules" means hard shell capsules (optionally containing medicament) each having telescopically engaged body and cap portions formed by a technique commonly known as the dipmolding technique (for example, see U.S. Pat. No. 3,173,840). The term "enteric capsules" means such capsules having enteric properties. Hydroxypropyl methylcellulose (National Formulary XIII) and cellulose acetate phthalate (U.S.P. XVIII) are sometimes referred to herein as HPMC and CAP, respectively. The term "hydroxypropyl methylcellulose phthalate" means a cellulose derivative which, like cellulose itself, is a polymeric, high molecular weight substance; and which has the following structural unit

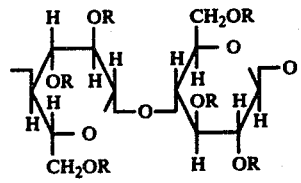

where R represents variously hydrogen, methyl, hydroxypropyl having the formula

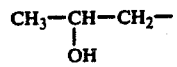

carboxybenzoyl having the formula

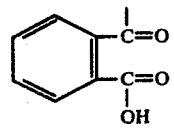

or 2-carboxybenzoyloxypropyl having the formula

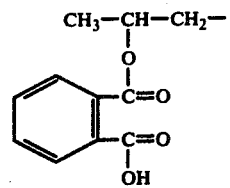

Hydroxypropyl methylcellulose phthalate is sometimes referred to herein as HPMCP.

For use in the invention, HPMCP typically has approximately 15-30% methoxyl content, 4-15% hydroxypropoxyl content, and 15-40% carboxybenzoyl content.

HPMCP can be prepared according to any of a number of methods. At the present time, at least two grades or types of HPMCP are commercially available from the Shinetsu Chemical Company of Tokyo, Japan. These grades or types are known as HP-50 and HP-55. HP-50 is stated to have 20-25% methoxyl content, 8-12% hydroxypropoxyl content, and 20-27% carboxybenzoyl content. HP-55 is stated to have 18-22% methoxyl content, 6-10% hydroxylpropoxyl content, and 27-35% carboxybenzoyl content. Both HP-50 and HP-55 are soluble in water by the addition of base. HP-50 is stated to dissolve above pH 5. HP-55 is stated to dissolve above pH 5.5.

The copolymer of methacrylic acid and methacrylic acid alkyl ester, sometimes referred to herein as MA acid/ester copolymer, has the following structural unit:

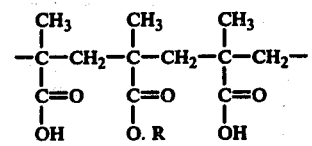

where R is a lower alkyl group, in particular, a methyl or ethyl group.

MA acid/ester copolymer can be prepared according to any of a number of methods. At least two grades or types of MA acid/ester copolymer are commercially available from Rohm & Haas Company of Tokyo, Japan. These grades or types are known as EUD-L and EUD-S. The acid value (amount of mg. of caustic potash needed to neutralize 1 gram of the dried substance) is stated as 292 for EUD-L and 178 for EUD-S. Both EUD-L and EUD-S are soluble in water when base is added. EUD-L is stated to dissolve above pH 6 and EUD-S above pH 7.

Ordinary pharmaceutical capsules made of gelatin do not have enteric properties and therefore when ingested do not reach the intestine while intact but instead rapidly dissolve or disintegrate in the acid secretions of the stomach. These is, however, a need for pharmaceutical capsules having enteric properties. In many cases, medicinal substances are more readily utilized and are of greater therapeutic value if they are absorbed from the upper portion of the intestine. Medical science has long sought to provide efficient means for rendering such substances available for absorption from the intestinal tract. This problem arises from the fact that many medicinals are either not absorbed from the stomach or rapidly destroyed on contact with the acid present in the stomach. Some examples of medicinals of this type are gland products and penicillin. Many medicinals, such as hog bile, quinacrine, sulfa drugs, and the like, also are very unpleasant to take and cause severe gastric disturbances which may be coupled with very unpleasant regurgitation of the drug. Another use for enteric capsules is to prevent the breakdown or dilution of drugs which are used for their effect in the intestinal tract, such as intestinal antiseptics or anthelmintics. It is obvious that there is a great need for a practical method of administering medicinals of the above types in a form having enteric properties.

Many attempts have been made heretofore to obtain suitable enteric capsules. In general, methods of manufacture for enteric capsules fall into one of two classes:

(I) Those comprising treating the exterior of the assembled filled capsule, for example with formalin to decrease the solubility of the capsule wall, or with a coating of an enteric substance;

(II) and those comprising forming the capsule parts by the dip-molding technique using a dipping solution which itself after drying possesses enteric properties.

The method according to the present invention falls under category II. Of the methods of this type, the use of CAP and of alkali metal salt of HPMCP is known in the art.

However, it has been found that capsules made using the dip-molding technique employing the known enteric dipping solutions often lack the elastic properties of gelatin and in some cases after aging lose their enteric properties.

It is an object of the present invention to provide improved enteric capsules.

It is also an object of the invention to provide enteric capsules having improved elasticity, i.e., freedom from brittleness.

It is a further object of the invention to provide enteric capsules having improved retention of enteric properties when subjected to prolonged storage.

It is still a further object of the invention to provide methods for manufacturing such improved enteric capsules.

The enteric capsules of the present invention, which advantageously meet these objects, have capsule body and cap portions formed by dip-molding using a homogeneous film-forming mixture comprising (1) gelatin and an ammonium salt of hydroxylpropyl methylcellulose phthalate polymer, or (2) hydroxypropyl methylcellulose and an ammonium salt of cellulose acetate phthalate polymer, or (3) gelatin and an ammonium salt of a copolymer of methacrylic acid and methacrylic acid alkyl ester optionally in combination with additional ingredients such as plasticizer and/or coloring agent.

In manufacturing enteric capsules in a series of steps according to the invention, CAP, HPMCP or MA acid/ester copolymer is first dissolved in a dilute aqueous solution of ammonium hydroxide. Sufficient ammonium hydroxide is used to effect complete solution; any excess is removed subsequently as described below. Gelatin or HPMC is then added to the resulting aqueous solution of the ammonium salt (of CAP, HPMCP or MA acid/ester copolymer) and is dissolved in any suitable way, optionally with heating, for a time sufficient to allow complete solution. The ratio of ammonium salt to gelatin or HPMC can be varied and is preferably 5 parts of ammonium salt by weight, measured as free acid form, to 1 to 5 parts by weight of gelatin or HPMC. Sufficient ammonium salt must be present in the finished capsule to render it insoluble in the stomach acid but the quantity must not be so great as to prevent the rapid dissolution of the capsule when it comes in contact with the alkaline contents of the intestine. The resulting solution, if necessary after heating to obtain the desired viscosity, is suitable for the production of capsule parts by the dip-molding procedure. If the solution contains excess ammonia or has foam, the same can be removed by heating the solution under slightly reduced pressure. The pH of the defoamed solution is about 6.4 to 7.8. For capsule production, suitable metal mold pins are dipped into the solution (free of foam) and the wet film thus formed on the pins upon lifting from the solution is dried gradually at 40° C. in the conventional way to obtain the desired hard shell capsule parts. The wall thickness of capsules produced by the dip-molding depends on the viscosity of the dipping solution. If a thin-walled capsule is desired more water is used, whereas if a thick-walled capsule is desired a more concentrated or viscous solution is used.

The wall thickness of the capsule is also dependent upon the temperature of the dipping solution. This factor, however, is maintained fairly constant since an appreciable change in temperature is necessary in order to produce a small change in wall thickness and it is undesirable from a practical standpoint to vary the temperature over large ranges. Therefore, the solution in the dipping pan is kept at a fairly constant temperature between about 32 and 49° C. and preferably in the neighborhood of about 35–37° C.

If desired, a coloring agent or a plasticizer may be added to our new enteric capsules without destroying or substantially altering their valuable chemical and physical properties. The same kinds of coloring agents as used in the usual hard shell capsules are suitable. Up to 5% (by weight of the dry gelatin or HPMC) of a plasticizer, such as glycerine or propylene glycol, may be added if desired.

The new enteric capsules are produced, as indicated above, by the dip-molding procedure. The accompanying drawing shows an empty hard shell capsule 10 of the invention, in elevation and partly cut away to expose the interior of the capsule. The capsule has a cap portion 11 and a body portion 12 having open ends 11a and 12a which portions are in telescopic engagement to provide, in conventional form, a closed sealed container adapted to be opened, filled with medicament powder or the like and reclosed in final finished form. The capsules can be made, if desired, with one or more locking features.

The new enteric capsules of the invention have excellent enteric properties and pharmaceutical acceptability. They are chemically and physically stable and do not develop significantly increased acidity during storage and use. In addition, they have a uniform wall thickness and a low percentage of manufacturing defects.

Although it is known in the prior art that the mentioned polymers have enteric properties and can be used for the surface coating of pharmaceutical formulations such as tablets and granules, it is surprising that satisfactory pharmaceutical capsules can be manufactured by incorporating the polymer throughout the capsule wall itself. This is because the commercial manufacture of pharmaceutical capsules is such a sensitive operation that it is adversely affected by almost any change in the conventional ingredients or operating conditions.

The invention is illustrated by the following examples.

EXAMPLE 1

Aqueous ammonium hydroxide (10%, 42 ml.) is diluted with 300 ml. of water and, stirring, 85 g. of HPMCP (grade HP-55) is added and dissolved. Gelatin (40 g.) is added to the resulting homogeneous solution and the mixture is allowed to stand to permit hydration and complete solution of the gelatin. The latter solution is heated to 60° C. and left standing overnight at room temperature. Then it is heated under a slightly reduced pressure to eliminate excess ammonia and to defoam the solution. In a typical procedure, the pH of the obtained solution was 7.4. For the formation of capsule halves by the dip-molding technique the homogeneous solution is placed in separate dipping pans (cap and body pans) maintained at respective temperatures of 36.7° C. and 34.4° C. Previously lubricated metallic cap and body mold pins are dipped into the dipping solutions thus obtained and are withdrawn and lifted slowly in conventional fashion to provide for even distribution of the liquid film layer over the effective area of each mold pin. The coated pins are then kept stationary for a sufficient period to gellify the film layer on the pin. The capsule halves thus formed are dried by blowing with dehumidified air at 15-16° C., and are removed from the pins, trimmed and joined together with the other halves of the capsule to provide the finished enteric hard shell capsules ready for filling.

As a demonstration that the capsules have the desired enteric properties, the same are subjected to a standard dissolution test of the type described in the Japanese Pharmacopeia, 8th Ed., 855-859, simulating conditions of the human body. To simulate the acid conditions in the stomach, an artificial gastric juice is used having a pH of about 1.2. It contains 2.0 g. of sodium chloride and 24.0 ml. of dilute hydrochloric acid diluted with water to a total volume of 1,000 ml. The alkaline conditions of the intestine are simulated by use of an artificial intestinal juice having a pH of about 7.5. It contains 35.8 g. of disodium hydrogen phosphate and 6.0 ml. of dilute hydrochloric acid diluted with water to a total volume of 1,000 ml. Both the acid and alkaline tests are carried out at 37±2° C. The empty gelatin/HPMCP ammonium salt capsules obtained according to the invention are filled with No. 2 Red lactose powder and banded with enteric seal, i.e., a material which is insoluble in artificial gastric juice and insoluble artificial intestinal juice. In a typical procedure when the resulting filled capsules were subjected to this dissolution test, they were found uniformly unchanged after 120 minutes in the first solution (artificial gastric juice, and when transferred to the second solution (artificial intestinal juice), the capsules completely disintegrated and dissolved within 5 to 10 minutes so that the capsule contents were thereby released exclusively in the alkaline environment.

EXAMPLE 2

Cellulose acetate phthalate (CAP, 50 g.) is dissolved in 220 ml. of 1.5% aqueous ammonium hydroxide and 50 g. of hydroxypropyl methylcellulose is added thereto. The mixture is heated to provide complete solution, and the resulting solution is heated under reduced pressure by the above-described method to remove excess ammonia; final pH, 6.6. Capsules are then prepared from the resulting HPMC/CAP ammonium salt enteric dipping solution by the above-described method and are filled and tested by the same method, typically with the same result, i.e., no dissolution when subjected to artificial gastric juice but complete dissolution and content release in the alkaline environment within a short exposure period.

EXAMPLE 3

Methacrylic acid/methacrylic acid ethyl ester copolymer (EUD-S, 96 g.) is dissolved in 400 ml. of 2% aqueous ammonium hydroxide and 27 g. of gelatin is added thereto. The mixture is allowed to stand to accomplish hydration of the gelatin and the resulting solution is heated to 60° C. and left standing overnight at room temperature. The foam and excess ammonia are removed by heating the solution under reduced pressure; final pH of the solution was 7.6. Capsules are prepared from this solution using the method described in Example 1. The empty capsules are filled and sealed in the same way and tested for enteric properties by the dissolution test as described. These MA acid/ester copolymer capsules typically meet the requirements of insolubility in gastric fluid and prompt solubility in intestinal fluid.

In other tests designed to show the enteric characteristics on aging, it was found that the capsules of the invention using ammonium salt as exemplified, unlike prior art enteric capsules, all pass the described enteric dissolution test. Thus, in the aging test simulating one year aging after manufacture (storage for 4 weeks at 40° C. under 40% relative humidity), the capsules of the present invention did not dissolve in gastric fluid but dissolved promptly in intestinal fluid. Also, these capsules when produced with coloring agents in the dipping solution did not undergo adverse color change under aging conditions. Moreover, the capsules had excellent retention of elasticity, transparency and lustre under aging. Significantly, the capsules were free of any tendency to generate any odor of ammonia under aging.

I claim:

1. A hard-shell pharmaceutical capsule comprising telescopically engaged body and cap portions having enteric properties, being characterized by relative freedom from brittleness and by substantial absence of degradation on exposure to artificial gastric juice for 120 minutes, and the body and cap portions being formed by the dip-moldng technique from a homogeneous film-forming composition comprising a member of the group consisting of
   (1) hydroxypropyl methylcellulose and an ammonium salt of cellulose acetate phthalate polymer, and
   (2) gelatin and an ammonium salt of a copolymer of methacrylic acid and methacrylic acid ester,
   the capsule having the proportion of 5 parts by weight of the ammonium salt, measured as free acid form, to 1 to 5 parts by weight of the gelatin or hydroxypropyl methylcellulose.

2. A pharmaceutical capsule according to claim 1 and containing up to 5% of glycerine.

3. A pharmaceutical capsule according to claim 1 and containing a coloring agent.

4. A pharmaceutical capsule according to claim 1 and containing up to 5% of propylene glycol.

5. A pharmaceutical capsule according to claim 1 formed from a homogeneous composition comprising hydroxypropyl methylcellulose and an ammonium salt of cellulose acetate phthalate polymer.

6. A pharmaceutical capsule according to claim 1 formed from a homogeneous composition comprising gelatin and an ammonium salt of a copolymer of methacrylic acid and methacrylic acid ester.

* * * * *